(12) United States Patent
Perusini

(10) Patent No.: US 12,274,761 B2
(45) Date of Patent: Apr. 15, 2025

(54) COMPOSITIONS AND METHODS TO DETECT GLUA1 IN BRAIN AND TO IDENTIFY THE PRESENCE OF GLUA1-MEDIATED PTSD

(71) Applicant: Neurovation Labs, Inc., New York, NY (US)

(72) Inventor: Jennifer Perusini, New York, NY (US)

(73) Assignee: Neurovation Labs, Inc., New York, NY (US)

( * ) Notice: Subject to any disclaimer, the term of this patent is extended or adjusted under 35 U.S.C. 154(b) by 766 days.

(21) Appl. No.: 17/569,139

(22) Filed: Jan. 5, 2022

(65) Prior Publication Data
US 2022/0125956 A1    Apr. 28, 2022

Related U.S. Application Data

(63) Continuation of application No. 16/080,412, filed as application No. PCT/US2017/019638 on Feb. 27, 2017, now Pat. No. 11,224,668.
(Continued)

(51) Int. Cl.
*A61K 51/04* (2006.01)
*A61K 31/13* (2006.01)
(Continued)

(52) U.S. Cl.
CPC .......... *A61K 51/0406* (2013.01); *A61K 31/13* (2013.01); *A61K 31/132* (2013.01);
(Continued)

(58) Field of Classification Search
CPC .. A61K 31/13; A61K 31/132; A61K 51/0406; C07B 59/001; C07C 209/74; C07C 211/19; C07C 2603/74
See application file for complete search history.

(56) References Cited

U.S. PATENT DOCUMENTS 6,406,868 B1   6/2002  Kamboj et al.
8,236,789 B2   8/2012  Nakashima et al.
(Continued)

FOREIGN PATENT DOCUMENTS

EP    2365974 B1    9/2011
EP    2806276 A1    11/2014

OTHER PUBLICATIONS

American Psychiatric Association, "Trauma- and Stressor-Related Disorders", Diagnostic and statistical manual of mental disorders (5th ed.), Arlington, VA, American Psychiatric Publishing (2013).
(Continued)

*Primary Examiner* — Gerald Johnson
(74) *Attorney, Agent, or Firm* — Amster, Rothstein & Ebenstein LLP

(57) ABSTRACT

The present invention provides compositions and methods for detecting GluA1, as a subunit protein and/or as a GluA1-containing, GluA2-lacking AMPAR complex. The invention further provides composition and methods for detecting and/or diagnosing PTSD. The invention further relates to compositions that can be detected using radiological imaging techniques, and processes for performing such imaging techniques using the compositions, to identify elevated GluA1 expression or activity in a subject, which is a biological marker of PTSD.

20 Claims, 4 Drawing Sheets

Related U.S. Application Data

(60) Provisional application No. 62/301,583, filed on Feb. 29, 2016.

(51) Int. Cl.
  *A61K 31/132* (2006.01)
  *C07B 59/00* (2006.01)
  *C07C 209/74* (2006.01)
  *C07C 211/19* (2006.01)

(52) U.S. Cl.
  CPC .......... *C07B 59/001* (2013.01); *C07C 209/74* (2013.01); *C07C 211/19* (2013.01); *C07C 2603/74* (2017.05)

(56) References Cited

U.S. PATENT DOCUMENTS

| | | |
|---|---|---|
| 2007/0218002 A1 | 9/2007 | Barrio et al. |
| 2011/0065766 A1 | 3/2011 | Wang et al. |
| 2018/0200391 A1* | 7/2018 | Takahashi .............. A61K 51/00 |

OTHER PUBLICATIONS

AMPA receptor, Wikipedia, https://en.wikipedia.org/wiki/AMPA_receptor, last accessed Dec. 16, 2016.

Bolshakov et al., Different arrangement of hydrophobic and nucleophilic components of channel binding sites in N-methyl-D-aspartate and AMPA receptors of rat brain is revealed by channel blockade, Neuroscience Letters 291 (2000) 101-104.

Choi et al., Low levels of methyl B-cyclodextrin disrupt GluA1-dependent synaptic potentiation but not synaptic depression, J. Neurochemistry, 2015, 132: 276-285.

Das et al., Increased AMPA receptor GluR1 subunit incorporation in rat hippocampal CA1 synapses during benzodiazepine withdrawal, J Comp Neurol. Dec. 20, 2008; 511(6): 832-846.

Heiss et al., Brain Receptor Imaging, The Journal of Nuclear Medicine, 2006, 47 (2): 302-312.

Magazanik et al., Block of open channels of recombinant AMPA receptors and native AMPA/kainate receptors by adamantane derivatives, Journal of Physiology (1997) 505.3, pp. 655-663.

Majo et al., PET and SPECT tracers for glutamate receptors, Drug Discovery Today, vol. 18, Issues 3-4, Feb. 2013, pp. 173-184, available at http://www.sciencedirect.com/science/article/pii/S1359644612003571.

Morris et al., Diagnostic accuracy of 18F amyloid PET tracers for the diagnosis of Alzheimer's disease: a systematic review and meta-analysis, Eur J Nucl Med Mol Imaging. 2016; 43: 374-385.

Olah et al., Ionic Fluorination of Adamantane, Diamantane, and Triphenylmethane with Nitrosyl Tetrafluoroborate/Pyridine Polyhydrogen Fluoride (PPHF), J. Org. Chem., 1983, 48 (19), pp. 3356-3358 (Sep. 1983) (DOI: 10.1021/io00167a050).

Park et al., Calcium-Permeable AMPA Receptors Mediate the Induction of the Protein Kinase A-Dependent Component of Long-Term Potentiation in the Hippocampus, Journal of Neuroscience, Jan. 13, 2016, 36 (2) 622-631.

Perusini et al., Induction and Expression of Fear Sensitization Caused by Acute Traumatic Stress, Neuropsychopharmacology, 41: 45-57 (2016).

Perusini, Jennifer Nicole, The Mechanisms of Fear Sensitization Caused by Acute Traumatic Stress: from Induction to Expression to Long-Lasting Reversal, UCLA: Psychology 0780 (2014), retrieved from: http://escholarship.org/uc/item/3578829d.

PTSD Statistics, PTSD United, available at http://www.ptsdunited.org/ptsd-statistics-2/.

Rau, V. & Fanselow, M. S. (2009). Exposure to a stressor produces a long lasting enhancement of fear learning in rats. Stress, 12, 25-33.

Rau, V., De Cola, J. P., & Fanselow, M. S. (2005). Stress-induced enhancement of fear learning: An animal model of posttraumatic stress disorder. Neuroscience & Biobehavioral Reviews, 29, 1207-1223.

Rozen and Gal, Direct Synthesis of Fluoro-Bicyclic Compounds with Fluorine, J. Org. Chem., 1988, 53 (12), pp. 2803-2807 (Jun. 1988) (DOI: 10.1021/jo00247a026).

Salabert et al., Radiolabeling of [18F]-fluoroethylnormemantine and initial in vivo evaluation of this innovative PET tracer for imaging the PCP sites of NMDA receptors, Nuclear Medicine and Biology 42 (2015) 643-653.

Tikhonov et al., Intersegment Hydrogen Bonds as Possible Structural Determinants of the N/Q/R Site in Glutamate Receptors, Biophysical Journal, vol. 77 (Oct. 1999), pp. 1914-1926.

Vandenberghe et al., AMPA Receptor Calcium Permeability, GluR2 Expression, and Selective Motoneuron Vulnerability, The Journal of Neuroscience, Jan. 1, 2000, 20(1):123-132, available at http://www.jneurosci.org/content/neuro/20/1/123.full.pdf.

Waxman et al., Society of Nuclear Medicine Procedure Guideline for FDG PET Brain Imaging, Ver. 1.0 (Feb. 8, 2009).

Weiss, Ca2+ Permeable AMPA Channels in Diseases of the Nervous System, Frontiers in Molecular Neuroscience 4 (2011): 42, PMC, Web. Aug. 24, 2017.

* cited by examiner

COMPOSITIONS AND METHODS TO DETECT GLUA1 IN BRAIN AND TO IDENTIFY THE PRESENCE OF GLUA1-MEDIATED PTSD

CROSS-REFERENCE TO RELATED APPLICATIONS

This application is a continuation of U.S. patent application Ser. No. 16/080,412, filed on Aug. 28, 2018, which is a U.S. national stage entry under 35 U.S.C. § 371 of PCT International Patent Application No. PCT/US17/19638, filed on Feb. 27, 2017, which claims the benefit of and priority to U.S. Provisional Application No. 62/301,583, filed on Feb. 29, 2016, the contents of each of which are incorporated by reference in their entirety as if fully set forth herein.

BACKGROUND OF THE INVENTION

Post-Traumatic Stress Disorder (PTSD) is an incapacitating psychiatric disorder that affects 7-10% of the U.S. population. It develops in 1 in 5 people that experience or witness a traumatic event, such as warfare, natural disasters, and abuse. In a given year, about 7.7 million adults (aged 18-54) will develop PTSD symptoms and at a given time, 24.4 million people have PTSD in the U.S. alone. According to the Department of Veterans Affairs, up to 10% of Gulf War veterans, 20% of Operation Enduring Freedom and Operation Iraqi Freedom veterans, and 30% of Vietnam War veterans have experienced PTSD symptoms. According to recent data, PTSD imposes an annual economic burden exceeding $42 billion, mostly due to misdiagnosis and under-treatment (1).

PTSD symptoms include avoiding stimuli associated with the traumatic event, constant re-experiencing of the event, and increased arousal, exhibited by exaggerated startle response. Under normal circumstances, these symptoms are adaptive for coping with the trauma. For instance, avoiding stimuli associated with the traumatic event lessens the probability of encountering the threat or others like it. However, patients with PTSD lose normal daily functioning because these responses become dysfunctional and exaggerated.

At present, there is no existing biological marker (or biomarker) for PTSD in humans and no objective detection systems or methods. Therefore, the only means for diagnosis of the disease are checklists of symptoms (e.g., using either the Structured Clinical Interview for DSM (SCID)—PTSD Module, or the Clinical Administered PTSD Scale (CAPS)/Life Events Checklist), modeled after symptoms listed in the Diagnostic and Statistical Manual for Mental Disorders (American Psychiatric Association, 2013) (2) (hereby incorporated by reference in its entirety as if fully set forth herein). PTSD is underdiagnosed, partially due to the fact that PTSD is difficult to detect with only checklists and self-report and partially because diagnoses are typically given long after the trauma and after negative effects have manifested in the patient.

By definition, conventional PTSD diagnosis requires manifestation of symptoms. The diagnostic criteria (DSM-V) include exposure to a traumatic stressor (criterion A), reexperiencing, avoidance/numbing, and hyperarousal symptoms (criteria B through D), duration of at least one month (criterion E), and clinically significant distress or impairment in social/occupational functioning (criterion F) (2).

Thus, there is a need in the art for compositions and methods for detecting and/or diagnosing PTSD, particularly at a physiological level. Relatedly, there is a need for compositions and methods of detecting in the brain molecular increases of certain proteins known to correspond to presence of PTSD and/or cause PTSD. There is a need for detecting PTSD or its molecular causes prior to manifestation of symptoms. There is also a need to treat PTSD once a detection and/or diagnosis has been made. Current treatments suppress select symptoms only and/or rely upon therapies to facilitate coping with PTSD, but a comprehensive treatment for PTSD that targets its physiological cause is lacking. The present invention satisfies these unmet needs.

SUMMARY OF THE INVENTION

The present invention is generally related to a new tracer, a radiolabeled ligand of GluA2-lacking, calcium permeable AMPA receptors (α-amino-3-hydroxy-5-methyl-4-isoxazolepropionic acid receptors or AMPARs) and/or GluA1-containing AMPARs, designed for use in radiological or nuclear imaging (e.g., diagnostic radiological imaging), which may detect PTSD.

The present invention provides a method of detecting PTSD in a subject, comprising administering to the subject a first amount of a radiolabeled composition comprising at least one ligand of a GluA1-containing, GluA2-lacking AMPAR labeled with a radioactive isotope, wherein the radiolabeled composition comprises the following structure:

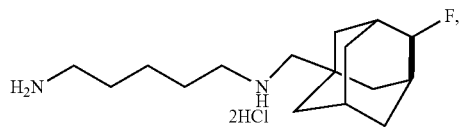

wherein the F is an [$^{18}$F] radioisotope.

The method further comprises creating at least one image of a brain of the subject using positron emission tomography (PET) or single-photon emission computed tomography (SPECT); and determining or quantifying from the at least one image a GluA1-containing, GluA2-lacking AMPAR density in the amygdala of the brain of the subject based at least in part upon an amount of the radiolabeled composition detected in the at least one image, and comparing the density so determined or quantified with a predetermined baseline level, wherein a density greater than the predetermined baseline level indicates PTSD in the subject.

Also provided is a method of detecting GluA1 levels, or GluA1-containing, GluA2-lacking AMPAR levels, in an amygdala of a subject, comprising administering to the subject a first amount of a radiolabeled composition comprising a ligand of GluA1 or a ligand of a GluA1-containing, GluA2-lacking AMPAR effective for detection of the radiolabeled composition in the amygdala of the subject using radiological imaging; and determining or quantifying, by the radiological imaging of the radiolabeled composition in the amygdala of the subject, GluA1 subunit density or GluA1-containing, GluA2-lacking AMPAR density in the amygdala of the subject.

Also provided is a method of detecting PTSD in a subject, comprising administering to the subject a first amount of a radiolabeled composition comprising a ligand of GluA1 or a ligand of a GluA1-containing, GluA2-lacking AMPAR effective for detection of the radiolabeled composition in an amygdala of the subject using radiological imaging; and determining or quantifying, by the radiological imaging of the radiolabeled composition in the amygdala of the subject, GluA1 subunit density or GluA1-containing, GluA2-lacking AMPAR density in the amygdala of the subject, and comparing the density so determined or quantified with a predetermined baseline level, wherein a density greater than the predetermined baseline level indicates PTSD in the subject.

Also provided is a method of detecting GluA1-mediated PTSD in a subject, comprising administering to the subject a first amount of a radiolabeled composition comprising a ligand of GluA1 or a ligand of a GluA1-containing, GluA2-lacking AMPAR effective for detection of the radiolabeled composition in an amygdala of a brain of the subject using radiological imaging; and determining or quantifying, by the radiological imaging of the radiolabeled composition in the amygdala of the subject, GluA1 subunit density or GluA1-containing, GluA2-lacking AMPAR density in the amygdala of the subject, and comparing the density so determined or quantified with a predetermined baseline level, wherein a density greater than the predetermined baseline level indicates GluA1-mediated PTSD in the subject.

The present invention also provides a method of detecting GluA1 levels (e.g., GluA1 protein levels), or GluA1-containing, GluA2-lacking AMPAR levels, in an amygdala of a subject comprising administering to the subject a first amount of a radiolabeled composition comprising at least one ligand of GluA1 labeled with a radioactive isotope or comprising at least one ligand of a GluA1-containing, GluA2-lacking AMPAR labeled with a radioactive isotope; creating at least one image of a brain of the subject using radiological imaging (e.g., PET, SPECT, or another radiological detection and/or imaging system and/or device); and determining or quantifying from the at least one image a GluA1 subunit density or a GluA1-containing, GluA2-lacking AMPAR density in the amygdala of the brain of the subject based at least in part upon an amount of the radiolabeled composition detected in the at least one image, so as to detect GluA1 protein levels, or GluA1-containing, GluA2-lacking AMPAR levels, respectively, in an amygdala of a subject.

Also provided is a method of detecting PTSD in a subject comprising administering to the subject a first amount of a radiolabeled composition comprising at least one ligand of GluA1 labeled with a radioactive isotope or comprising at least one ligand of a GluA1-containing, GluA2-lacking AMPAR labeled with a radioactive isotope; creating at least one image of a brain of the subject using PET or SPECT or another radiological detection and/or imaging device; and determining or quantifying from the at least one image a GluA1 subunit density or a GluA1-containing, GluA2-lacking AMPAR density in an amygdala of the brain of the subject based at least in part upon an amount of the radiolabeled composition detected in the at least one image. In embodiments, the method may further comprise comparing the density so determined or quantified with a predetermined baseline level, wherein a density greater than the predetermined baseline level indicates PTSD in the subject. The method may further comprise providing a diagnosis for PTSD based at least in part upon a determination of whether the GluA1 subunit density or the GluA1-containing, GluA2-lacking AMPAR density in the amygdala exceeds the predetermined baseline level by at least a threshold amount.

The present invention provides a method of treating PTSD in a subject comprising receiving information indicating a detection of elevated levels of GluA1, either alone as a subunit protein or in GluA1-containing, GluA2-lacking calcium permeable AMPAR complexes in an amygdala of the subject, wherein the detection has been obtained by administering to the subject an amount of a radiolabeled composition comprising at least one radiolabeled ligand of GluA1 or comprising at least one radiolabeled ligand of a GluA1-containing, GluA2-lacking AMPAR, the amount of the radiolabeled composition effective to detect the radiolabeled composition in the amygdala of the subject using radiological imaging (e.g., PET or SPECT); determining or quantifying GluA1 levels or GluA1-containing, GluA2-lacking AMPAR levels in the amygdala of the subject; and determining that the GluA1 levels or the GluA1-containing, GluA2-lacking AMPAR levels exceed a predetermined baseline level. The method of treating further comprises administering to the subject an amount of a treatment composition effective to treat PTSD.

In embodiments, the administered treatment composition is effective to reduce GluA1 expression levels or GluA1-containing, GluA2-lacking AMPAR expression levels in the amygdala of a subject. In embodiments, the administered treatment composition is effective to block GluA1-containing, GluA2-lacking AMPARs in the amygdala of a subject. In embodiments, the administered treatment composition is effective to inhibit receptor function of GluA1-containing, GluA2-lacking AMPARs in the amygdala of the subject.

The present invention also provides a composition comprising at least one radiolabeled detector of a GluA1-containing, GluA2-lacking calcium permeable (α-amino-3-hydroxy-5-methyl-4-isoxazolepropionic acid) receptor.

Also provided is a composition comprising at least one radiolabeled detector of GluA1 protein.

Also provided is a compound having the following structure:

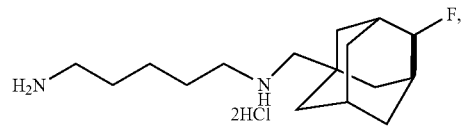

wherein the F is an [$^{18}$F] radioisotope.

Also provided is a compound having the following structure:

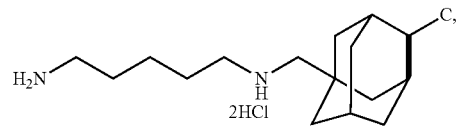

wherein the C is a [$^{11}$C] radioisotope.

Also provided is a compound having the following structure:

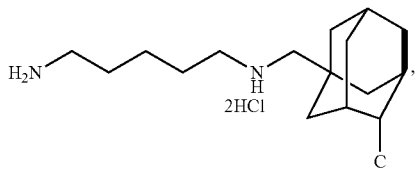

wherein the C is a [$^{11}$C] radioisotope.

The present invention provides a method of producing a radiolabeled compound comprising performing a radiofluorination reaction on a first compound having the following structure:

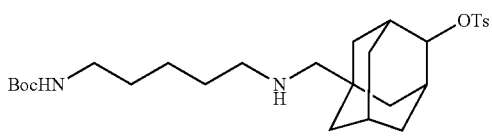 [SMILES: Cc1ccc(S(=O)(=O)OC2C3CC4CC2CC(CNCCCCCNC(=O)OC(C)(C)C)(C4)C3)cc1]

so as to produce a second compound having the following structure:

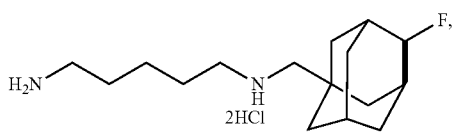

wherein the F is an [$^{18}$F] radioisotope.

A method of synthesizing a radiolabeled compound is provided, which comprises obtaining (e.g., producing and/or trapping) an amount of [$^{18}$F]; eluting the [$^{18}$F] with a phase transfer catalyst KF/K2.2.2 so as to produce a solution of [$^{18}$F]KF/K2.2.2 complex; adding a first compound having the following structure:

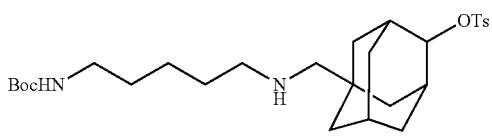 [SMILES: Cc1ccc(S(=O)(=O)OC2C3CC4CC2CC(CNCCCCCNC(=O)OC(C)(C)C)(C4)C3)cc1]

to the solution of [$^{18}$F]KF/K2.2.2 complex so as to perform a radiofluorination reaction to create a second compound having the following structure:

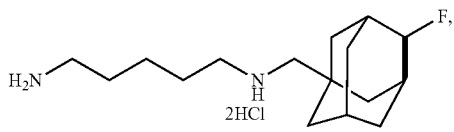

wherein the F is an [$^{18}$F] radioisotope. In embodiments, the method may further comprise purifying the reaction contents from to produce a purified compound radiolabeled with [$^{18}$F]. In embodiments, purifying the reaction contents can comprise performing radio-HPLC on the product of the radiofluorination reaction.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1A:
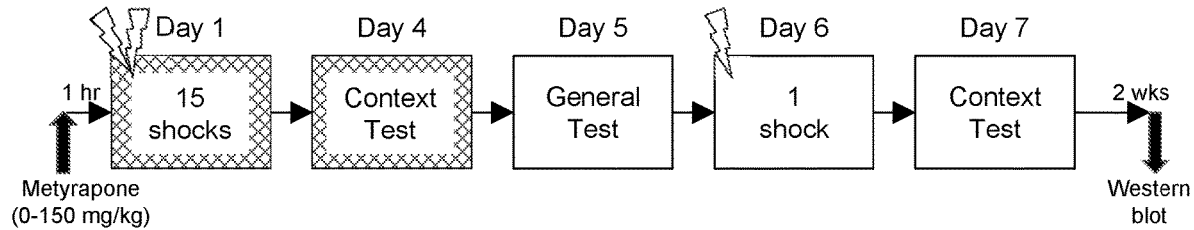
FIG. 1A illustrates an experimental design for Stress-Enhanced Fear Learning (SEFL), a rodent model of PTSD.

The present invention relates generally to compositions and methods for detecting levels (e.g., densities) of GluA1 (also referred to as GluR1), either alone as a subunit protein or within GluA1-containing, GluA2-lacking AMPAR complexes in an amygdala of a subject (e.g., a human subject). In embodiments, the compositions and methods of the present invention can enable detection and/or diagnosis of PTSD in a subject. The compositions and methods may comprise use of imaging techniques (e.g., diagnostic and/or radiological imaging techniques) involving imaging agents designed to target GluA1 and/or GluA1-containing and/or GluA2-lacking AMPARs in the brain.

AMPARs are composed of four types of protein subunits, which are designated as GluA1, GluA2 (also referred to as GluR2), GluA3 (also referred to as GluR3), and GluA4 (also referred to as GluR4) (3). The HUGO gene nomenclature committee refers to the encoding gene for GluA1 as HGNC: 4571, and for GluA2 as HGNC:4572. GluA1 is at times referred to by the gene name, GRIA1, which produces GluA1 protein when translation is activated (e.g., by a learning event). The GRIA2 gene produces GluA2 protein when translation is activated. Non-limiting exemplary GRIA1 sequences include NCBI Reference Sequences: NM000827.3, NM001258023.1 and NM001258022.1. Non-limiting exemplary GRIA2 sequences include NCBI Reference Sequences: NM000826.3, NM001083620.1, and NM001083619.1.

The AMPAR subunits combine to form tetramers, protein polymers composed of four monomer units. The presence of a GluA2 subunit will almost always render the receptor channel impermeable to calcium, meaning that the neurons on which these AMPARs are located are more difficult to depolarize, transduce signals, and/or communicate with neighboring neurons. Without cell activity, GluA2/GluA3-containing AMPARs are more commonly located at the synapse because of their stability to be tethered to the cell membrane. On the other hand, GluA1-containing AMPARs are important for cell plasticity and are brought to cell synapses in the presence of cell activity to strengthen cell connections. GluA1-containing AMPARs that are lacking GluA2 are commonly found in areas important for learning and memory and particularly fear learning and memory, such as the hippocampus and the amygdala. Enrichment of synaptic GluA2-lacking AMPARs (presumably GluA1 homomers), as well as synaptic insertion of GluA1 in these regions underlies long-term potentiation (LTP), a process by which recent patterns of activity cause persistent strengthening of synapses, which is crucial for long-term memory formation. Blocking the formation of GluA1 protein will effectively block the formation of functional GluA1-containing AMPARs after a learning event and/or potentially block LTP/long-term memory formation (4).

A composition is provided comprising at least one radiolabeled detector of GluA1, either alone as a subunit protein or as part of a GluA1-containing, GluA2-lacking calcium permeable (α-amino-3-hydroxy-5-methyl-4-isoxazolepropionic acid) receptor complex, which may be a human AMPAR. Accordingly the composition may comprise at least one radiolabeled detector of a GluA1-containing, GluA2-lacking calcium permeable AMPAR. The radiolabeled detector may comprise a ligand of a GluA1-containing, GluA2-lacking calcium permeable AMPAR. In embodiments, a composition may comprise at least one radiolabeled detector of GluA1 protein, e.g., as a subunit protein. In embodiments, the radiolabeled detector may be a detector of GluA1 expression, surface expression, AMPAR activity, or a combination thereof. In embodiments, the radiolabeled detector may be an inhibitor of AMPAR function. In embodiments, such an inhibitor may be an inhibitor of calcium permeable AMPAR function.

In embodiments, the radiolabeled detector may be selected from the group consisting of a nucleic acid, an antisense nucleic acid (e.g., GluA1 ASO), a ribozyme, a peptide, a small molecule (e.g., a molecule of an organic compound having a low molecular weight (e.g., less than 900 daltons) that may help regulate a biological process, with a size on the order of 1 nm), an antagonist, an aptamer, and a peptidomimetic. The radiolabeled detector may comprise a radioisotope, such as $[^{18}F]$ or $[^{11}C]$.

In embodiments, the radiolabeled detector may comprise N'-[(4-fluoro-1-adamantyl)methyl]pentane-1,5-diamine. In embodiments, the radiolabeled detector may comprise the following structure:

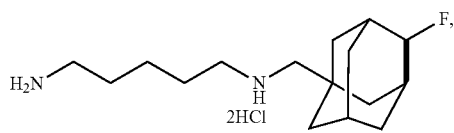

wherein the F is an $[^{18}F]$ isotope.

In embodiments, the radiolabeled detector may comprise the following structure:

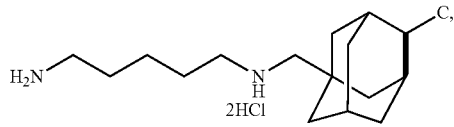

wherein the C is a $[^{11}C]$ isotope.

In embodiments, the radiolabeled detector may comprise the following structure:

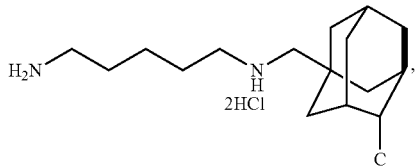

wherein the C is a $[^{11}C]$ isotope.

In embodiments, the composition may comprise a solution of the radiolabeled detector, such as a saline solution and/or an ethanol solution. In embodiments, a solution comprising the radiolabeled detector may be diluted, e.g., with water or saline. The composition may be put into a solution, e.g., for administration.

In embodiments, the composition can serve as a radiolabeled tracer in an imaging detection process, e.g., radiological or nuclear imaging, such as PET, SPECT, or other radiological sensing and/or imaging, such as using a portable sensing device. In embodiments, the imaging detection process may be used to quantify and/or determine expression (e.g., levels, amounts, and/or densities) of GluA1 protein or of GluA1-containing, GluA2-lacking AMPARs in an amygdala of a subject. In embodiments, amygdala refers to both a left amygdala and a right amygdala together. In embodiments, only a portion of the amygdala is studied, imaged, and/or examined, such as the left portion or the right portion, which may include one or more nuclei on either side of the amygdala, such as the BLA. Accordingly, a BLA may be examined, which may be a left BLA, a right BLA, or both a left and a right BLA. In embodiments, the subject is a human subject. In embodiments, the imaging detection process may be used to determine whether the GluA1 protein itself or the GluA1-containing, GluA2-lacking AMPARs exceed a predetermined baseline level. In embodiments, the imaging detection process may be used to determine a degree to which and/or an amount by which the GluA1 protein or the GluA1-containing, GluA2-lacking AMPARs exceed a predetermined baseline level. In embodiments, the imaging detection process may be usable to detect PTSD in a subject, e.g., based on detected levels (e.g., densities) of GluA1, either alone as a subunit protein or in GluA1-containing, GluA2-lacking calcium permeable AMPAR complexes in an amygdala of a subject, and/or further based upon a comparison to one or more baseline levels (e.g., baseline densities) or threshold levels.

In embodiments, a baseline or predetermined baseline level (e.g., of GluA1 levels or GluA1-containing, GluA2-lacking AMPAR levels (e.g., density)) may be determined by performing the imaging detection process on a plurality of subjects known not to be suffering from PTSD; determining respective amygdalar GluA1 levels or GluA1-containing, GluA2-lacking AMPAR levels, in each of the plurality of subjects; and computing as the predetermined baseline level a normalized average of the respective amygdalar GluA1 levels or GluA1-containing, GluA2-lacking AMPAR levels in each of the plurality of subjects.

In embodiments, the predetermined baseline level (e.g., of GluA1 levels (e.g., density) or of GluA1-containing, GluA2-lacking AMPAR levels (e.g., density)) may be determined by performing the imaging detection process on a first plurality of subjects known not to be suffering from PTSD; determining first respective amygdalar GluA1 density or GluA1-containing, GluA2-lacking AMPAR density in each of the first plurality of subjects; computing a first normalized average of the first respective amygdalar GluA1 density or GluA1-containing, GluA2-lacking AMPAR density; performing the imaging detection process on a second plurality of subjects known to be suffering from PTSD; determining second respective amygdalar GluA1 density or GluA1-containing, GluA2-lacking AMPAR density in each of the second plurality of subjects; computing a second normalized average of the second respective amygdalar GluA1 density or GluA1-containing, GluA2-lacking AMPAR density; and determining as the predetermined baseline level an amygdalar GluA1 density or GluA1-containing, GluA2-lacking AMPAR density based at least in part upon the first normalized average and the second normalized average. Determining the baseline may comprise performing one or more study replications and/or comparing across many subjects, e.g., using statistical analyses.

A compound is provided having the following structure:

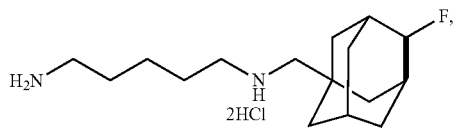

wherein the F is an F-18 radioisotope.

A compound is provided having the following structure:

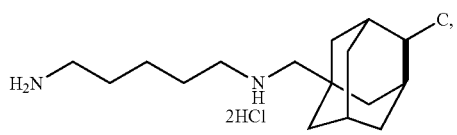

wherein the C is a [$^{11}$C] radioisotope.

A compound is provided having the following structure:

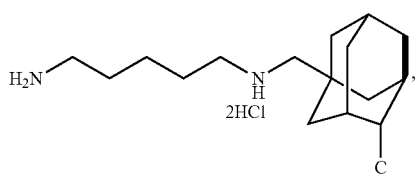

wherein the C is a [$^{11}$C] radioisotope.

The present invention provides a method of detecting PTSD in a subject, comprising administering to the subject a first amount of a radiolabeled composition comprising at least one ligand of a GluA1-containing, GluA2-lacking AMPAR labeled with a radioactive isotope, wherein the radiolabeled composition comprises the following structure:

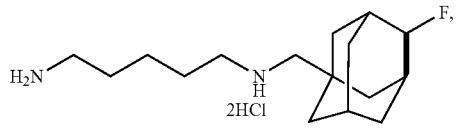

wherein the F is an [$^{18}$F] radioisotope.

The method further comprises creating at least one image of a brain of the subject using radiological imaging (e.g., PET or SPECT); and determining or quantifying from the at least one image a GluA1-containing, GluA2-lacking AMPAR density in the amygdala of the brain of the subject based at least in part upon an amount of the radiolabeled composition detected in the at least one image, and comparing the density so determined or quantified with a predetermined baseline level, wherein a density greater than the predetermined baseline level indicates PTSD in the subject.

A method of detecting GluA1, either alone as a subunit protein or in GluA1-containing, GluA2-lacking calcium permeable AMPAR complexes in the amygdala of a subject is provided. In embodiments, the method of detecting GluA1 (e.g., GluA1 levels and/or GluA1 subunit density) or GluA1-containing, GluA2-lacking AMPARs (e.g., GluA1-containing, GluA2-lacking AMPAR levels and/or density) may comprise administering to the subject a first amount of a radiolabeled composition (e.g., a tracer or radiotracer) comprising a ligand of GluA1 or a ligand of a GluA1-containing, GluA2-lacking AMPAR effective for detection of the radiolabeled composition in the amygdala of the subject using radiological imaging (e.g., PET or SPECT); and determining or quantifying, by the radiological imaging of the radiolabeled composition in the amygdala of the subject, GluA1 subunit density or GluA1-containing, GluA2-lacking AMPAR density in the amygdala of the subject.

A method of detecting PTSD (e.g., GluA1-mediated PTSD) in a subject is provided. The method may comprise administering to the subject a first amount of a radiolabeled composition comprising a ligand of GluA1 or a ligand of a GluA1-containing, GluA2-lacking AMPAR effective for detection of the radiolabeled composition in an amygdala of a brain of the subject using radiological imaging; and determining or quantifying, by the radiological imaging of the radiolabeled composition in the amygdala of the subject, GluA1 subunit density or GluA1-containing, GluA2-lacking AMPAR density in the amygdala of the subject, and comparing the density so determined or quantified with a predetermined baseline level, wherein a density greater than the predetermined baseline level indicates PTSD (e.g., GluA1-mediated PTSD) in the subject. In embodiments, such an evaluation using the detection methods of the present invention may be performed after a subject experiences a trauma and/or before manifestation of symptoms (e.g., observable symptoms). In embodiments, the subject is a subject who experienced a trauma and/or a subject being evaluated for presence of and/or severity of PTSD. In embodiments, evaluation for PTSD may be performed before, during, and/or after treatment, and/or multiple times during the course of a treatment regimen.

In embodiments, the ligand is a ligand of GluA1. In such cases, the process may determine GluA1 levels, such as GluA1 subunit density. In embodiments, the ligand is a ligand of a GluA1-containing, GluA2-lacking AMPAR. In such cases, the process may determine GluA1-containing, GluA2-lacking AMPAR levels and/or density. In embodiments, the radiological imaging is PET or SPECT imaging. In embodiments, the radiological imaging comprises using another radiation sensing, detection, and/or imaging device. Such a device may be a portable device, such as a handheld electronic device. Accordingly, the radiological imaging may comprise using a portable electronic device to detect radiation levels associated with the radiolabeled composition (e.g., associated with an amount of the radiolabeled composition that has undergone uptake and accumulation in the amygdala). In embodiments, such a device may comprise a cellular phone and/or an integrated camera. The radiation sensing device may have installed thereon non-transitory computer-readable memory or otherwise be operable with particularly programmed software, which can evaluate detected radiation levels, e.g., to provide an indication or notification of such levels and/or to provide an indication or notification that such levels exceed a preprogrammed baseline level. Such software may comprise an installable application, such as a downloadable or an uploadable application.

In embodiments, determining or quantifying GluA1 subunit density and/or levels of GluA1-containing, GluA2-lacking AMPAR density and/or levels in the amygdala of the subject can comprise determining or quantifying an amount of the radiolabeled composition in the amygdala after administration. In embodiments, determining or quantifying GluA1 subunit density or GluA1-containing, GluA2-lacking AMPAR density in the amygdala of the subject can comprise detecting, determining, quantifying, visualizing, and/or estimating radioactive emissions of the radiolabeled composition in the amygdala after administration. Detectable and/or measurable radioactive emissions may provide a proxy for detecting and/or measuring GluA1 itself or GluA1-containing, GluA2-lacking AMPARs, via receptor binding of the ligands. Accordingly, radioactive emissions may estimate GluA1 levels and/or GluA1-containing/GluA2-lacking AMPAR density, according to the respective ligand used. Radioactive emissions of the administered radiolabeled composition may be detected, quantified visualized, and/or estimated following an uptake period of time after or during which the composition can accumulate and/or bind to its target GluA1 protein or GluA1-containing, GluA2-lacking AMPARs. Such radioactive emissions from the radiolabeled composition or a portion thereof (e.g., the portion that bound to targets in an area of interest and/or area to be imaged) may be detected by a special-purpose camera or imaging device that can produce pictures, provide molecular information, and/or provide indications of detected radiation levels, e.g., indicating the locations of such detected radiation.

In embodiments, the method may further comprise comparing the radiolabeled composition in the amygdala after administration to a control amount. In embodiments, the method may further comprise comparing the radioactive emissions of the radiolabeled composition in the amygdala after administration to a control (e.g., a control image, a control amount or control level or control density, or a control density representation, to name a few). In embodiments, the method may comprise comparing receptor density associated with the radioactive emissions to a control receptor density. In embodiments, a control density representation may comprise a visual representation of a control amount of GluA1 or of GluA1-containing, GluA2-lacking AMPARs in an amygdala, which may be a particular subject's amygdala (e.g., with a visual representation of the control amount overlaid thereon) or an artistic rendering of an amygdala with the control amount. Such a visual representation may be generated (e.g., by particularly programmed software) and/or provided to technicians, doctors, and/or other personnel, and/or used for diagnostic purposes.

The control amount and/or the control receptor density may be a predetermined baseline level, which baseline may be determined as described herein. In embodiments, the baseline level may be associated with a particular radiolabeled composition. In embodiments, the control amount may be an amount or estimation of radioactive emissions from an amygdala. In embodiments, the control amount may be an amount, level, and/or density of GluA1 protein or of GluA1-containing, GluA2-lacking AMPARs. In embodiments, the method may further comprise comparing the emissions of the radiolabeled composition in the amygdala after administration to a reference brain region or other organ with a known or approximately known GluA1 amount or GluA1-containing, GluA2-lacking AMPAR amount. In embodiments, the method may comprise using an uptake value, such as a standardized uptake value and/or a fractional uptake value, to determine levels of GluA1, either alone as a subunit protein or in GluA1-containing, GluA2-lacking calcium permeable AMPAR complexes.

A method of detecting GluA1, either itself (e.g., detecting the GluA1 protein subunit itself, whether isolated or not isolated from other compositions) in an amygdala of a subject or as part of a GluA1-containing, GluA2-lacking AMPAR complex in the amygdala of the subject is provided. In embodiments, the method is a method of detecting GluA1 protein levels, or of GluA1-containing, GluA2-lacking AMPAR levels, in an amygdala of a subject. In embodiments, the method may determine or detect elevated GluA1 levels and/or that GluA1 levels are not elevated (e.g., at or around baseline or below baseline). The method comprises administering to the subject a first amount of a radiolabeled composition comprising at least one ligand of GluA1 labeled with a radioactive isotope or comprising at least one ligand of a GluA1-containing, GluA2-lacking AMPAR labeled with a radioactive isotope; creating at least one image of a brain of the subject or a region thereof (e.g., the amygdala, such as the left amygdala and/or the right amygdala) using radiological imaging (e.g., PET or SPECT); and determining or quantifying from the at least one image a GluA1 level (e.g., GluA1 subunit density) or GluA1-containing, GluA2-lacking AMPAR level (e.g., density level) in the amygdala of the brain of the subject based at least in part upon an amount of the radiolabeled composition (e.g., an amount of selective uptake and accumulation of the radiolabeled composition in the brain) detected and/or detectable in the at least one image and/or an amount of radioactive emissions detected.

Accordingly, the method may comprise administering to the subject a first amount of a radiolabeled composition comprising at least one ligand of GluA1 labeled with a radioactive isotope or comprising at least one ligand of a GluA1-containing, GluA2-lacking AMPAR labeled with a radioactive isotope; creating at least one image of a brain of the subject using PET or SPECT; and determining or quantifying from the at least one image a GluA1 subunit density or a GluA1-containing, GluA2-lacking AMPAR density in the amygdala of the brain of the subject based at least in part upon an amount of the radiolabeled composition detected in the at least one image, e.g., so as to detect GluA1 protein levels, or GluA1-containing, GluA2-lacking AMPAR levels, respectively, in an amygdala of a subject.

The present invention provides a method of detecting PTSD (e.g., GluA1-mediated PTSD) in a subject, comprising administering to the subject a first amount of a radiolabeled composition comprising at least one ligand of GluA1 labeled with a radioactive isotope or comprising at least one ligand of a GluA1-containing, GluA2-lacking AMPAR labeled with a radioactive isotope; creating at least one image of a brain of the subject using PET or SPECT or another radiological detection and/or imaging device; and determining or quantifying from the at least one image a GluA1 subunit density or a GluA1-containing, GluA2-lacking AMPAR density in an amygdala of the brain of the subject based at least in part upon an amount of the radiolabeled composition detected in the at least one image. In embodiments, the method may further comprise comparing the density so determined or quantified with a predetermined baseline level, wherein a density greater than the predetermined baseline level indicates PTSD (e.g., GluA1-mediated PTSD) in the subject.

In embodiments, the radiolabeled composition can serve as an imaging agent composition, e.g., to enable and/or to facilitate radiological imaging, such as via PET or SPECT. In embodiments, the amount of the radiolabeled composition detected and/or detectable in the at least one image comprises an amount of radioactive emissions detected, e.g., detected in the amygdala. Accordingly, the methods of detection provided herein may comprise determining or quantifying from the at least one image a GluA1 level or GluA1-containing, GluA2-lacking AMPAR level in the amygdala of the brain of the subject based at least in part upon a detected amount of radioactive emissions, e.g., from the amygdala. The radioactive emissions correspond to a portion of the first amount of the radiolabeled composition that has undergone selective uptake and accumulation, e.g., by binding to GluA1 itself or to GluA1-containing, GluA2-lacking AMPARs, respectively.

In embodiments, the methods of detection may be performed and/or the first amount of the radiolabeled composition may be administered to the subject at least one hour after the subject experiences a trauma (e.g., a physical trauma and/or a mental trauma) and/or many years after the trauma, e.g., for as long as PTSD symptoms persist. Each patient may be given more than one scan (e.g., using the detection methods of the present invention) during his or her lifetime. In embodiments, the at least one image of the brain may be created between 15 minutes and 3 hours following administration of the radiolabeled composition.

In embodiments, the methods of detection may further comprise determining whether GluA1, either alone as a subunit protein or as part of a GluA1-containing, GluA2-lacking AMPAR complex in the amygdala exceeds a predetermined baseline level, which baseline may be determined as described herein. In embodiments, the methods may further comprise providing a diagnosis for PTSD based at least in part upon the determination of whether GluA1 levels (e.g., GluA1 subunit density) or GluA1-containing, GluA2-lacking AMPAR levels (e.g., density) in the amygdala exceeds the predetermined baseline level by at least a threshold amount. In embodiments, the threshold amount is zero, and the baseline is a GluA1-containing, GluA2-lacking AMPAR level over which the subject has elevated levels of GluA1-containing, GluA2-lacking AMPARs corresponding to PTSD levels. In embodiments, the threshold amount may be a percentage amount greater than a baseline level of non-PTSD subjects, which percentage amount may fall in the range of 5-10%, 5-15%, or 5-25%, to name a few. In embodiments, the threshold amount may be a numeric amount of GluA1-containing, GluA2-lacking AMPARs greater than a baseline level of non-PTSD subjects. The threshold for indicating, determining, and/or diagnosing PTSD may be determined by comparison (e.g., statistical analysis) of measured levels of GluA1-containing, GluA2-lacking AMPAR in respective amygdalae of control subjects and of subjects suffering from PTSD.

A method of treating PTSD in a subject is provided. The method comprises receiving information indicating a detection of elevated levels of GluA1, either alone as a subunit protein or in GluA1-containing, GluA2-lacking calcium permeable AMPAR complexes in an amygdala of the subject, wherein the detection has been obtained by administering to the subject an amount of a radiolabeled composition comprising at least one radiolabeled ligand of GluA1 or comprising at least one radiolabeled ligand of a GluA1-containing, GluA2-lacking AMPAR, the amount of the radiolabeled composition effective to detect the radiolabeled composition in the amygdala of the subject using radiological imaging (e.g., PET or SPECT); determining or quantifying GluA1 levels or GluA1-containing, GluA2-lacking AMPAR levels in the amygdala of the subject; and determining that the GluA1 levels or the GluA1-containing, GluA2-lacking AMPAR levels exceed a predetermined baseline level, which may be determined as described herein. The method further comprises administering to the subject an amount of a treatment composition effective to treat PTSD.

In embodiments, the treatment composition comprises a GluA1-containing, GluA2-lacking AMPAR ligand. In embodiments, the treatment composition comprises an inhibitor of calcium permeable AMPAR function.

In embodiments, the administered treatment composition (e.g., the respective amount of the treatment composition) is effective to reduce GluA1 expression levels (e.g., thereby blocking the formation of functional GluA1-containing AMPARs) or GluA1-containing, GluA2-lacking AMPAR expression levels in the amygdala of a subject. In embodiments, the administered treatment composition is effective to block GluA1-containing, GluA2-lacking AMPARs in the amygdala of the subject. In embodiments, such a treatment composition may be selected from the group consisting of a nucleic acid, an antisense nucleic acid, a ribozyme, a peptide, a small molecule, an inhibitor of GluA1 expression or synthesis, an aptamer, and a peptidomimetic.

In embodiments, the respective amount of the treatment composition is effective to inhibit receptor function of GluA1-containing, GluA2-lacking AMPARs in the amygdala of the subject. In embodiments, such a treatment composition may be selected from the group consisting of a peptide, a small molecule, an antagonist, an inhibitor, and a peptidomimetic. In embodiments, such a treatment composition may alleviate one or more symptoms of PTSD.

In embodiments, the radiolabeled composition is a radiolabeled detector or otherwise may have any of the properties and/or structures as described herein with respect to radiolabeled detectors. The radiolabeled composition may comprise a saline and/or ethanol solution.

In embodiments, the radiolabeled composition may be administered to the subject via injection into the bloodstream (e.g., intravenous injection and/or intravenous drip), via injection into tissue and/or an organ, via enema, orally (e.g., in pill, tablet, or liquid form), via inhalation, and/or via a nasal spray, in a manner effective to enter the amygdala of the subject.

In embodiments, the amount of the radiolabeled composition administered to the subject (e.g., the first amount) comprises a mass dose of the radiolabeled composition in a range of 0.0001 pg to 1 ng per kg of body weight of the subject. In embodiments, such a mass dose may fall in the range 0.01-2 pg/kg. In embodiments, an amount of radioactivity associated with the amount of the radiolabeled composition administered to the subject falls in a range of 1 to 2000 MBq. In embodiments, such a radioactivity level may fall in a range of 1-150 MBq, 100-250 MBq, 200-300 MBq, 150-370 MBq, 300-400 MBq, or 400-2000 MBq, to name a few. In some embodiments an effective radiation dose equivalent associated with the amount of the radiolabeled composition administered to the subject falls in a range of 1 to 100 µSv, which is linearly related to radioactivity. In embodiments, the radiation dosages may fall in a range of 1-12 µSv, 10-25 µSv, 20-30 µSv, 30-40 µSv, to name a few.

Administration of the radiolabeled composition (and/or a solution thereof) in accordance with the present invention may occur in one bolus administered some time (e.g., an uptake period) before the detection and/or imaging takes place. However, in embodiments, the administration of the agents of the invention may be essentially continuous over a preselected period of time, may comprise in a series of spaced doses, or may comprise a singly administered dose, depending on factors known to skilled practitioners. Both local and systemic administration are contemplated. The amount administered may vary depending on various factors including, but not limited to, the composition chosen, a particular target being evaluated (e.g., GluA1 protein or GluA1-containing, GluA2-lacking AMPARs), a particular disease being evaluated (e.g., PTSD, anxiety, to name a few), the weight, the physical condition, and/or the age of the subject. Such factors can be determined by a clinician employing animal models or other test systems which are well known to the art. An effective amount of a composition for use in an imaging diagnostic procedure may be an amount sufficient to be detected by the imaging procedure, e.g., PET technique via detection of radioactive emissions, or may be an amount sufficient to bind to a target receptor.

When the radiolabeled ligands of the invention are prepared for administration, they may be combined with a pharmaceutically acceptable carrier, diluent, or excipient to form a pharmaceutical formulation, or unit dosage form.

In embodiments, an uptake period during which the radiolabeled composition travels through a body of a subject may be in the range of 5 to 100 minutes, 45 to 60 minutes, or 45 to 90 minutes, to name a few. Accordingly, an uptake period may be 5 minutes, 15 minutes, 30 minutes, 45 minutes, 50 minutes, 60 minutes, 80 minutes, 85 minutes, or 90 minutes, to name a few. An image acquisition time or a scan duration for a radiological imaging procedure (e.g., a PET scan or a SPECT scan) may be in the ranges of 5 to 45 minutes, 15 to 60 minutes, 30 to 60 minutes, or 30 to 90 minutes, to name a few, such as scan durations of 5 minutes, 10 minutes, 15 minutes, 20 minutes, or 30 minutes, to name a few. In embodiments, shorter scan durations may be performed, such as using a portable radiological sensing and/or imaging device.

In certain aspects the present invention relates to detecting an increase in the expression, surface expression, and/or activity of GluA1, an AMPAR subunit, by using specially designed imaging agent compositions. In certain embodiments, the method relates to detecting the activity of GluA2-lacking, calcium-permeable AMPARs, which are primarily composed of GluA1 subunits.

In one aspect of the present invention, a composition is created by radiolabeling a ligand for use with radiological imaging (e.g., PET or SPECT) or other diagnostic imaging systems and processes, the specific ligand being designed to bind with GluA1-containing and/or GluA2-lacking AMPARs, preferentially in an amygdala of a subject's brain.

In embodiments, the present invention comprises a method for diagnosing PTSD in a subject using a radiolabeled composition that is a ligand for a particular biomarker as an imaging agent (e.g., diagnostic imaging agent) and/or tracer for determining presence of and/or quantifying levels of the biomarker. The invention utilizes radiological (e.g., PET or SPECT) imaging, a technique that allows for the identification of molecular and cellular levels, such as brain receptor levels (e.g., density), in living humans. The technique may enable determination of changes in such levels. The imaging process uses small amounts of radiolabeled compounds (e.g., radiolabeled with positron-emitting isotopes, such as [$^{18}$F]fluorine, [$^{124}$I]iodine, or [$^{11}$C]carbon) having high specificity for the target molecule, chemical, protein, or other target of interest; radiolabeled compounds having high affinity (e.g., in pM and/or nM range) are needed for such measurements. The invention comprises at least one ligand of GluA1-containing and/or calcium permeable AMPARs labeled with a radioactive isotope. PET scanning or other radiological detection and/or imaging of a subject using this composition can reveal sites of high receptor concentration (e.g., AMPAR density). In embodiments, such sites can include the amygdala in the brain.

In embodiments, the diagnostic imaging agent is a ligand of AMPAR function. In embodiments, the ligand is an inhibitor of GluA2-lacking, calcium permeable and/or GluA1-containing AMPAR function. In embodiments, the composition comprises IEM-1460 (e.g., radiolabeled with a radioisotope such as [$^{11}$C]). In embodiments, the composition comprises IEM-1925 dihydrobromide. In embodiments, the composition comprises philanthotoxin 74. In embodiments, the composition comprises Naspm trihydrobromide. In embodiments, the ligand is an agonist of GluA2-lacking, calcium permeable and/or GluA1-containing AMPAR function. In embodiments, the composition comprises Cl-HIBO.

In embodiments, the present invention provides a composition for detecting PTSD in a subject. In embodiments, the composition comprises a radiolabeled ligand of GluA2-lacking, calcium permeable AMPARs and/or GluA1-containing AMPARs. In embodiments, the composition is a diagnostic imaging agent. In embodiments, the composition comprises a radiolabeled ligand of AMPAR function. In embodiments, the ligand is a radiolabeled inhibitor of calcium permeable and/or GluA1-containing AMPAR function. In embodiments, the ligand is a radiolabeled agonist of calcium permeable and/or GluA1-containing AMPAR function. In embodiments, the radiolabeled inhibitor is an inhibitor of calcium-permeable AMPAR, such as IEM-1460. In embodiments, the radiolabeled ligand is an agonist of calcium permeable AMPARs, such as Cl-HIBO.

In embodiments, the present invention provides a method for diagnosing PTSD. In embodiments, the method comprises administering a ligand of a GluA1-containing and/or GluA2-lacking AMPAR labeled with a radioactive isotope to a subject in a diagnostic imaging setting and detecting levels of GluA1-containing and/or GluA2-lacking AMPARs by proxy of radioactive emissions from the ligand labeled with the radioactive isotope. In certain embodiments, the composition comprises a ligand of GluA1 expression, surface expression, activity, or a combination thereof that has been labeled with a radiolabeled isotope to detect expression levels in the brain. These compounds may be radiolabeled with positron-emitting isotopes, including but not limited to [$^{18}$F]fluorine, [$^{124}$I]iodine, [$^{11}$C]carbon, [$^{15}$O]oxygen, [$^{13}$N]nitrogen, or [$^{76}$Br]bromide, using organic chemistry and/or radiochemistry methods.

In embodiments, a method for detecting PTSD can comprise administering to a human subject (e.g., orally or via intravenous injection) an imaging agent composition comprising at least one ligand of GluA1 labeled with a radioactive isotope. Such a composition is not found in nature and is markedly different from naturally occurring molecules. The imaging agent composition may be designed to bind with GluA1-containing and/or GluA2-lacking AMPARs. The method can further comprise creating at least one image of the brain of the human subject using PET or SPECT, or any other radiological imaging method; determining from the at least one image a GluA1 receptor density (which may be a density range) in the amygdala of the brain of the human subject based at least in part upon an amount of the imaging agent composition detectable in the at least one image; determining whether the GluA1-containing and/or GluA2-lacking AMPAR density in the amygdala exceeds a predefined baseline level of GluA1; and providing a diagnosis for PTSD based at least in part upon the determination of whether the GluA1-containing and/or GluA2-lacking AMPAR density in the amygdala exceeds the predefined baseline level by at least a threshold amount.

In certain embodiments, the method comprises detecting GluA1-containing and/or GluA2-lacking, calcium permeable AMPARs specifically in the left and/or right BLA of the subject. In certain embodiments, the method comprises administering a composition that is directed or targeted to the BLA.

In certain embodiments, the method comprises administering the composition to a subject who may have PTSD or is at risk for developing PTSD. For example, in certain embodiments, the method comprises administering the radiolabeled ligand and performing PET or SPECT scan imaging on a subject who has experienced a traumatic event. Exemplary traumatic events include but are not limited to, violence, assault, military experiences, accidents or near-accidents, natural disasters, and the like. In embodiments, the detection method is a diagnostic method. In embodiments, the diagnostic is performed within a defined period after the traumatic event. For example, in certain embodiments, the radiolabeled ligand is administered and PET scan is performed within minutes, hours, days (e.g., 1-3 days), weeks, months, or years after the traumatic event.

In embodiments, the present invention provides a composition for diagnosing PTSD in a subject. For example, in certain embodiments, the composition is used to detect PTSD in a subject that has experienced a trauma.

In embodiments, the composition comprises a ligand of and/or inhibitor of GluA1-containing and/or GluA2-lacking, calcium permeable AMPARs. For example, in embodiments, the composition inhibits GluA1 expression, GluA1 surface expression, GluA1 activity, or a combination thereof. In embodiments, the ligand and/or inhibitor is radiolabeled with a radioactive isotope.

In embodiments, the composition inhibits the activity of GluA1 including GluA1-containing AMPARs. In embodiments, the inhibitor inhibits the activity of GluA2-lacking, calcium permeable AMPARs. In certain embodiments, the inhibitor inhibits ionic influx through the AMPAR; inhibits agonist binding of the AMPAR; inhibits pore opening of the AMPAR; enhances pore blocking of the AMPAR; inhibits calcium influx of the AMPAR; or a combination thereof.

An inhibitor of GluA1 is any compound, molecule, or agent that reduces, inhibits, or prevents the function of GluA1. For example, an inhibitor of GluA1 is any compound, molecule, or agent that reduces GluA1 expression, surface expression, activity, or a combination thereof. In certain embodiments, the inhibitor inhibits the transcription of DNA, inhibits the translation of RNA, and/or inhibits the protein itself. In embodiments, an inhibitor of GluA1 comprises a peptide, an antibody, a small molecule, a ribozyme, an antagonist, an aptamer, a peptidomimetic, or any combination thereof.

In embodiments, the composition comprises an agonist of GluA1-containing and/or GluA2-lacking calcium permeable AMPARs. For example, in one embodiment, the composition activates GluA1 expression, GluA1 surface expression, GluA1 activity, or a combination thereof.

In embodiments, the composition stimulates the activity of GluA1 including GluA1-containing AMPARs. In embodiments, the agonist activates the activity of GluA2-lacking, calcium permeable AMPARs. In certain embodiments, the agonist increases ionic influx through the AMPAR; inhibits antagonist binding of the AMPAR; increases pore opening of the AMPAR; reduces pore blocking of the AMPAR; increases calcium influx of the AMPAR; or a combination thereof.

An agonist of GluA1 is any compound, molecule, or agent that increases or stimulates the function of GluA1. For example, an agonist of GluA1 is any compound, molecule, or agent that increases GluA1 expression, surface expression, activity, or a combination thereof. In certain embodiments, the agonist increases the transcription of DNA, increases the translation of RNA, or activates the protein itself. In embodiments, an agonist of GluA1 comprises a peptide, an antibody, a small molecule, a ribozyme, an antagonist, an aptamer, a peptidomimetic, or any combination thereof.

The present invention relates generally to compositions and methods for diagnosing PTSD in a subject using diagnostic imaging techniques. In certain aspects the present invention relates to detecting an increase in the expression, surface expression, and/or activity of GluA1, an AMPAR subunit. In certain embodiments, the method relates to detecting the activity of GluA2-lacking calcium permeable AMPARs, which are primarily composed of GluA1 subunits.

In one aspect, the present invention provides a method for diagnosing PTSD in a subject, comprising administering at least one radiolabeled inhibitor of GluA1-containing or calcium permeable AMPARs and detecting GluA1-containing or calcium permeable AMPARs, e.g., via radioactive emissions.

In embodiments, the present invention provides a method for diagnosing PTSD. In embodiments, the method comprises administering a ligand of a GluA1-containing or GluA2-lacking, calcium permeable AMPAR labeled with a radioactive isotope to a subject in a diagnostic imaging setting and measuring radioactive emissions from a portion of a brain (e.g., the amygdala) of the subject. For example, in certain embodiments, a composition that is administered to a subject comprises a ligand of GluA1 expression, surface expression, activity, or a combination thereof that has been labeled with a radiolabeled isotope to detect expression levels in the brain. In embodiments, the composition comprises a ligand of a GluA1-containing or calcium permeable AMPAR labeled with a radioactive isotope. In certain embodiments, the method comprises detecting GluA1-containing or GluA2-lacking, calcium permeable AMPARs specifically in the BLA of the subject. In certain embodiments, the method comprises administering a composition that is directed or targeted to the BLA.

In embodiments, the present invention provides a method for diagnosing PTSD by performing a PET scan using a radiolabeled GluA1-containing and/or GluA2-lacking, calcium permeable AMPAR ligand in a subject who has experienced a trauma. In embodiments, the method comprises diagnosing PTSD by performing a PET scan using a radiolabeled GluA1-containing and/or GluA2-lacking, calcium permeable AMPAR ligand to a subject having a genetic predisposition to developing PTSD. In embodiments, the method comprises diagnosing PTSD by performing a PET scan using a radiolabeled GluA1-containing and/or GluA2-lacking, calcium permeable AMPAR ligand to a subject who has experienced a traumatic event. In certain embodiments, the subject has been the victim of, or a witness to, a traumatic event, including, but not limited to, violence, assault, sexual assault, accident, vehicle accident, near accident, natural disaster, military violence, or the like.

In certain embodiments, the method comprises diagnosing PTSD by performing a PET scan using a radiolabeled GluA1-containing and/or GluA2-lacking, calcium permeable AMPAR ligand in a defined time period following the traumatic event. For example, in certain embodiments, the method comprises diagnosing PTSD by performing a PET scan using a radiolabeled GluA1-containing and/or GluA2-lacking, calcium permeable AMPAR ligand within 1 day, 2 days, 3 days, 5 days, 7 days, 10 days, 2 weeks, 4 weeks, 1 month, 2 months, 3 months, 6 months, 9 months, 1 year, 2 years, 5 years, or 10 years following the traumatic event, to name a few. The detection methods of the invention may be used to diagnose PTSD in any subject. In embodiments, the subject is a mammal, including, but not limited to, a human, primate, cow, horse, sheep, goat, dog, cat, rodent, and the like.

Labeling a GluA1-containing and/or GluA2-lacking, calcium permeable AMPAR ligand with a radioactive isotope can be done using any method known to the skilled artisan. Performing a PET scan using a radiolabeled GluA1-containing and/or GluA2-lacking, calcium permeable AMPAR ligand can be done using any method known to the skilled artisan. A GluA1 ligand may therefore be a compound that inhibits or activates GluA1 function, activity, or stability. A GluA1 ligand may be any type of compound, including but not limited to, peptide, a small molecule, or combinations thereof. GluA1-containing and/or GluA2-lacking, calcium permeable AMPA receptor specific binding may be accomplished either directly or indirectly. Methods of decreasing or increasing expression of GluA1 include, but are not limited to, methods that use a ribozyme, a peptide, a small molecule, and combinations thereof.

Administration of a radiolabeled GluA1-containing or GluA2-lacking, permeable AMPAR ligand and detecting radioactive emissions therefrom can be used along with a treatment or treatment regimen to determine subjects requiring treatment, track treatment progress, and/or determine when treatment is no longer needed.

In embodiments, a radiolabeled GluA1-containing and/or GluA2-lacking, calcium permeable AMPAR ligand is administered to a subject, and radioactive emissions are detected and/or quantified. The ligand may also be a hybrid or fusion composition to facilitate, for instance, delivery to target cells or efficacy. In embodiments, a hybrid composition may comprise a tissue-specific targeting sequence. For example, in embodiments, the ligand is targeted to the BLA of the subject.

EXAMPLES

INTRODUCTION

Rodent experiments have suggested a link between upregulation of GluA1 in the amygdala of a subject and PTSD. Using a rodent model of PTSD called SEFL, it has been shown that after a traumatic event, there are enduring increases in GluA1 protein in the BLA (5, 6) (hereby incorporated by reference in their entireties as if fully set forth herein). However, other glutamate receptor subunits, such as the GluA1 subunit of the AMPAR and GluN1 subunit of the NMDAR, do not show any long-term changes (FIGS. 1A-D).

FIG. 1A illustrates an experimental design using SEFL (7, 8). Protein levels were measured using Western blot, an analytical technique to detect specific proteins in tissue samples.

Figure 1B:
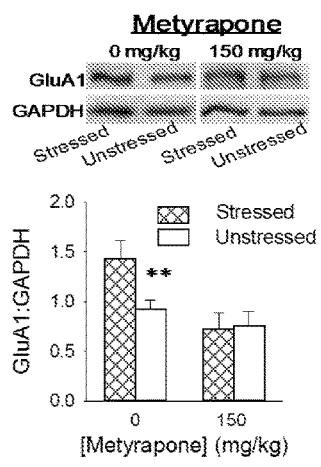
FIGS. 1B-D depict representative Western blot images and graphs of relative optical density ratios (±standard error of the mean (SEM)) of GluA1, GluA2, and GluN1, respectively, and a glyceraldehyde 3-phosphate dehydrogenase (GAPDH) control. These figures show the results of example experiments demonstrating that there are observed long-term increases in GluA1 protein in the basolateral amygdala (BLA) after a traumatic event. Glutamate receptor protein changes were measured three weeks after the initial trauma via Western blotting. While the GluA2 subunit of the AMPAR and the GluN1 subunit of the N-methyl-D-aspartate receptor (NMDAR) remained unchanged after trauma, GluA1 increased substantially. Metyrapone, a cortisol/corticosterone-synthesis blocker given before the trauma effectively preventing SEFL also prevented GluA1 increases and conferred levels to that of unstressed controls.

FIG. 1B depicts representative Western blot images of GluA1 and a control, GAPDH, from the BLA of stressed and unstressed rats, measured three weeks after the trauma. The graph shows mean GluA1: GAPDH optical density ratios (±SEM). GluA1 protein levels in the BLA were significantly higher in stressed rats than in unstressed rats and metyrapone-treated rats; (**$p<0.01$, two-way analysis of variance (ANOVA), followed by a priori planned comparisons) (5).

Figure 1C:
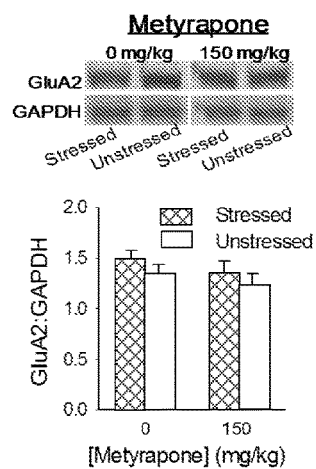

FIG. 1C depicts representative Western blot images of GluA2 and GAPDH from the BLA of stressed and unstressed rats, measured three weeks after the trauma. The graph shows mean GluA2: GAPDH optical density ratios (±SEM). Neither stress nor metyrapone had an effect on GluA2 levels (5).

Figure 1D:
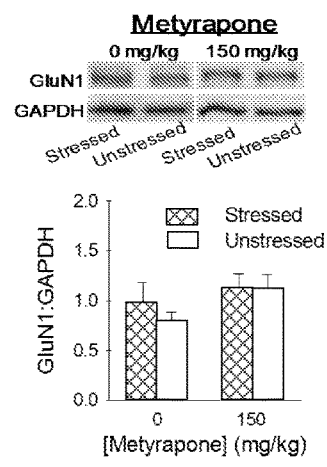

FIG. 1D depicts representative Western blot images of GluN1 and GAPDH from the BLA of stressed and unstressed rats, measured three weeks after the trauma. The graph shows mean GluN1: GAPDH optical density ratios (±SEM). Neither stress nor metyrapone had an effect on GluN1 levels (5).

Figure 2A:
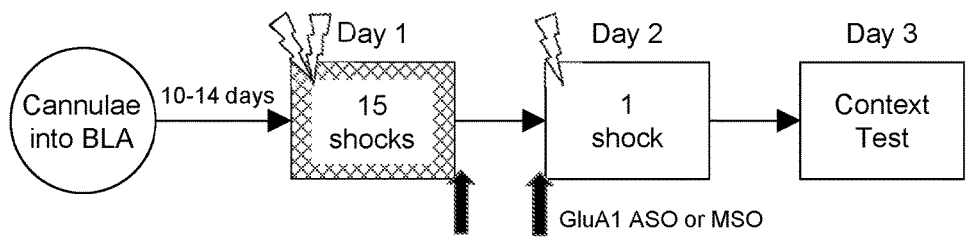
FIG. 2A illustrates an abbreviated SEFL experimental design.
Figure 2B:
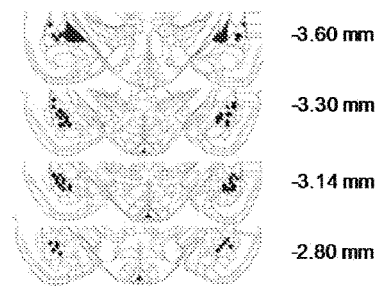
FIG. 2B illustrates cannulae placement into the basolateral amygdala (BLA) of rodents.
Figure 2C:
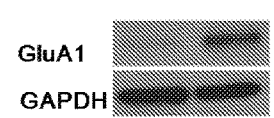
FIGS. 2C-E depict the results of example experiments demonstrating that intra-BLA infusions of GluA1 antisense oligonucleotide (ASO) after the 15-shock stressor reverse the SEFL. Delivering GluA1 ASO post-trauma significantly decreased GluA1 protein levels in stressed rats. Missense oligonucleotide (MSO) control infusions still conferred high level of GluA1 protein, as determined by Western blotting (FIGS. 2C-D) GluA1 ASO post-trauma also prevented the sensitized fear (i.e., freezing) typically observed in novel Context B after just a mild shock (labeled in the graph as the conditioning context) after receiving a trauma in context A (FIG. 2E).
Figure 2D:
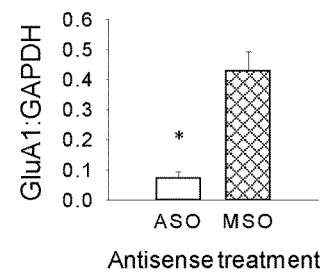
Figure 2E:
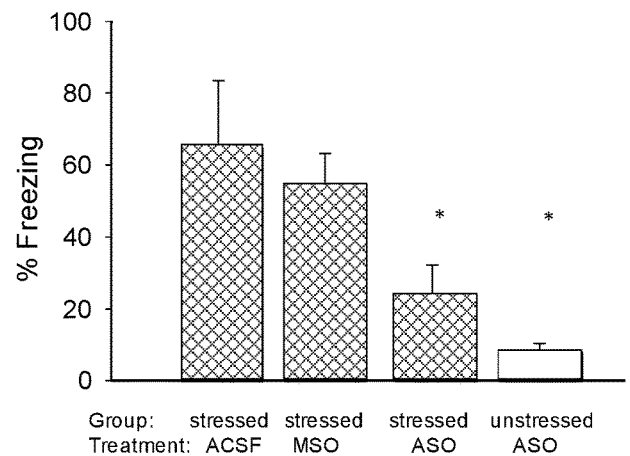

Because GluA1 increases are observed weeks after the trauma, post-trauma GluA1 ASO infusions directly into the BLA prevented sensitized fear responses usually observed in SEFL (FIGS. 2A-E) (5). FIG. 2A illustrates the experimental design, and FIG. 2B shows the cannulae placement. FIG. 2C depicts representative Western blot images of GluA1 and GAPDH from the BLA of stressed/MSO and stressed/ASO rats. FIG. 2D depicts mean GluA1: GAPDH optical density ratios (±SEM) from the BLA of stressed/MSO and stressed/ASO rats. ASO significantly lowers GluA1 levels in the BLA when delivered after the trauma compared with MSO (*$p<0.05$, one-way ANOVA). FIG. 2E depicts mean (±SEM) percent freezing in Context B on Day 3. GluA1 ASO significantly reduces conditional freezing compared with stressed controls (i.e., those infused with artificial cerebrospinal fluid (ACSF) or MSO) when delivered into the BLA post-trauma to unstressed levels (* $p<0.05$, one-way ANOVA followed by planned comparisons).

Figure 3A:
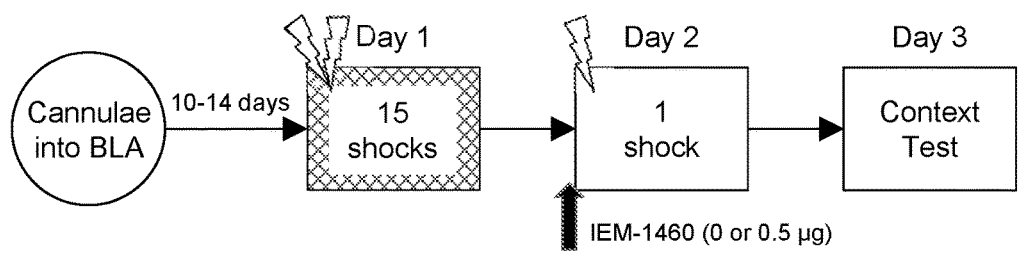
FIG. 3A illustrates a SEFL experimental design.
Figure 3B:
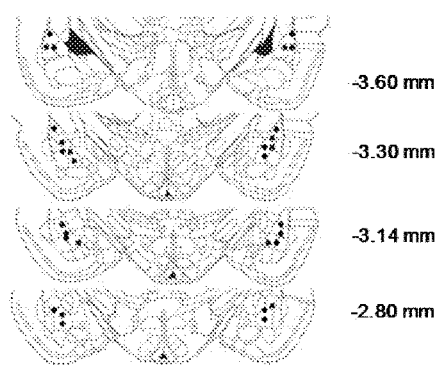
FIG. 3B illustrates cannulae placement verification in the BLA.
Figure 3C:
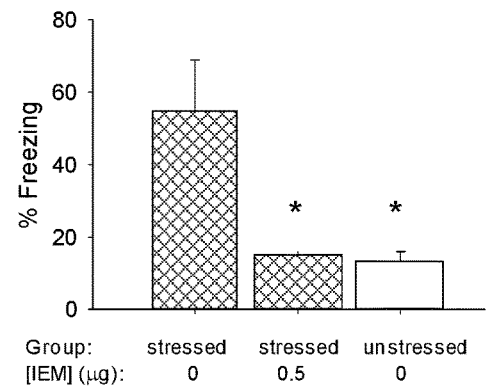
FIG. 3C depicts the results of example experiments demonstrating that intra-BLA infusions of IEM-1460, a selective GluA2-lacking AMPAR antagonist, after the 15-shock stressor attenuate SEFL. Blocking GluA2-lacking AMPARs in the amygdala post-trauma block the sensitized fear (i.e., freezing) typically observed in novel Context B after just a mild shock (labeled in the graph as the conditioning context) after receiving a trauma in Context A.

Similar results were observed using IEM-1460, a GluA2-lacking, GluA1-containing AMPAR antagonist, suggesting that the GluA1 subunit increase also increased viable GluA1-containing AMPARs to act upon (FIGS. 3A-C) (5). FIG. 3A depicts a SEFL experimental design, and FIG. 3B shows cannulae placement verification. FIG. 3C depicts mean freezing (±SEM) in Context B on Day 3. IEM-1460 infused post-trauma significantly reduces freezing in Context B compared with stressed rats infused with ACSF and unstressed controls (* p<0.05, one-way ANOVA, followed by a priori planned comparisons) (5).

This work discussed hereinabove was conducted in rodents using Western blotting techniques to detect glutamate receptor protein levels. Western blotting to detect specific proteins in humans is not viable in living subjects; it requires using post-mortem tissue and artificial antibodies to react with the target protein in this tissue. The present invention provides alternative methods to detect GluA1 protein levels utilizing nuclear imaging, which can be performed in live human patients. Instead of designing antibodies to react with the target protein in the tissue sample, nuclear imaging requires injecting a radioisotope with specificity to the protein that will also be able to penetrate the region of interest in awake patients. In particular for the present invention, nuclear imaging can be effected by radiolabeling a ligand of GluA1 or of GluA1-containing, GluA2-lacking AMPARs, such as those used in the outlined studies. While IEM-1460 is a known ligand of GluA1-containing, GluA2-lacking AMPARs, radiolabeling this compound directly with [$^{18}$F] in a manner that preserves its ability to bind to GluA1 is not feasible.

Difficulty of Radiolabeling

The most direct extrapolation of the example studies would be to radiolabel an already existing and commercially available drug that binds to GluA1-containing/GluA2-lacking AMPARs, such as IEM-1460 (N,N,H,-Trimethyl-5-[(tricyclo[3.3.1.13,7]dec-1-ylmethyl)amino]-1-pentanaminium-bromide hydrobromide). IEM-1460 or any other GluA2-lacking AMPAR ligands have never before been radiolabeled.

Figure 4:
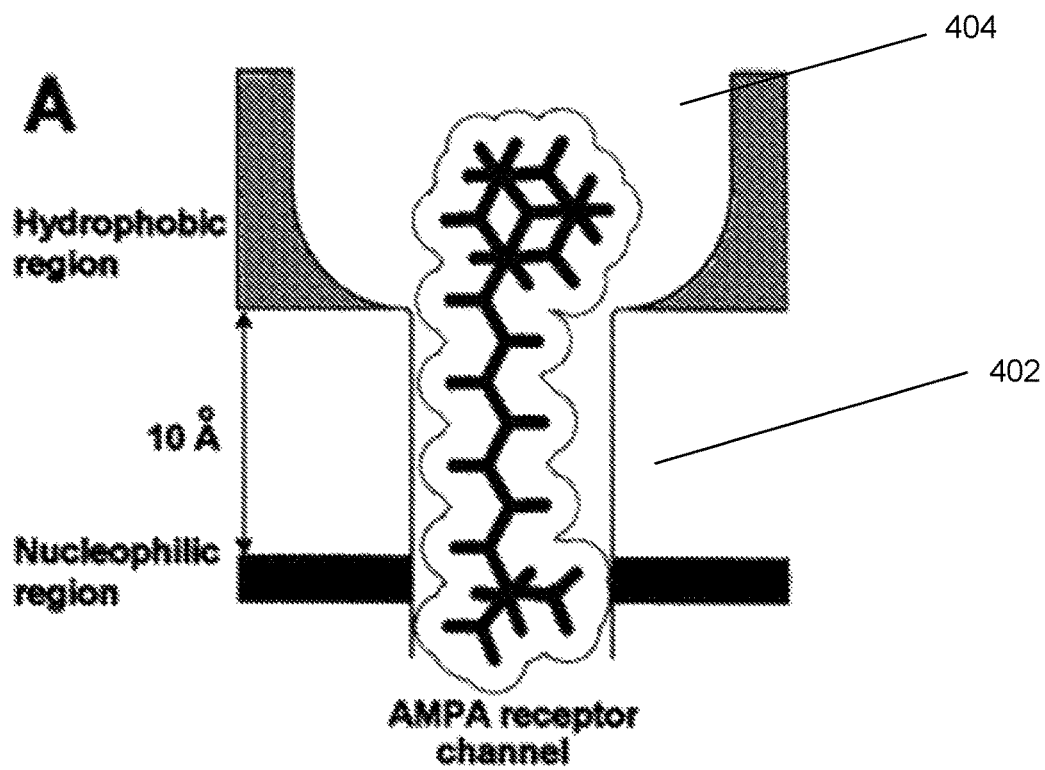
FIG. 4 illustrates a topographical model of channel binding sites in AMPARs. Hydrophobic and nucleophilic regions in the receptor are separated by approximately 10Å. Therefore, only compounds possessing a 'head and tail' structure such as IEM-1460 can block the channel.

Radiolabeling such a ligand is complicated by the necessity to add the radioisotope at a particular location of the structure so as not to interfere with and/or prevent binding. FIG. 4 illustrates exemplary AMPAR channel binding sites (9). Ligands of AMPARs have similar 'head and tail' structures with two primary structural features. The quaternary amine on the alkyl chain 402 is thought to associate with the pore region of ionotropic channels as a cation mimic. The adamantane portion 404 of the molecule is a hydrophobic moiety that fills space in the pore and confers the steric hindrance that prevents cation passage through the pore, According to Bolshakov et al., the terminal ammonium group is important for binding; and the chain length is crucial to allow binding to calcium permeable AMPARs (9). Chain length between adamantane moiety and terminal ammonium should be approximately 10 Å so that the adamantane can interact with the hydrophobic region at the pore of the receptor; while the ammonium group can interact with the nucleophilic region of the receptor.

In embodiments, [$^{11}$C] labeling of IEM-1460 may be possible. However, the [$^{18}$F] radioisotope is preferred to [$^{11}$C] for radiolabeling because its half-life of about 110 minutes is much greater than the approximately 20-minute half-life of [$^{11}$C]. Because of its short half-life, has severely limited clinical usability, requiring an on-site cyclotron to perform the labeling (10). There are some radiometals suitable for clinical use (e.g., [$^{68}$Ga]) but these are connected to the tracer via large/complex chelators and this would impact the pharmacologic properties of the product rendering it unusable for labeling AMPAR ligands.

A strategy for [$^{18}$F] labeling has not previously been discussed or proposed. IEM-1460 does not contain any halogen atoms. Direct fluorination of the product would most likely target the nucleophilic alkyl amine chain. Interfering with the alkyl amine would likely affect channel pharmacology by altering the nitrogen basicity. While IEM-1460 has been fluorinated with [$^{19}$F] in the past, the conditions used are not compatible with [$^{18}$F] radiolabeling (11, 12).

Given that direct fluorination of IEM-1460 is unfavorable and/or infeasible in terms of preserving its ability and/or specificity to bind to AMPARs, incorporating [$^{18}$F] into the compound or otherwise creating a radiolabeled ligand of AMPARs and in particular GluA2-lacking AMPARs presents technical challenges.

Method of Manufacture

Figure 5:
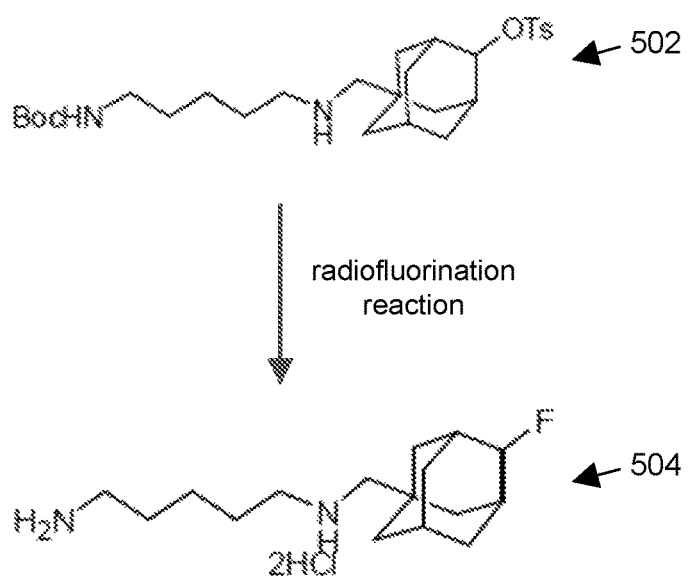
FIG. 5 is a flowchart illustrating an exemplary process for synthesizing a radiolabeled composition in exemplary embodiments of the present invention.

A radiolabeling process was developed to produce a radiolabeled compound that is a ligand of GluA1 or of GluA1-containing, GluA2-lacking AMPARs with a radiolabel a radioisotope) in a location that does not prevent binding to the AMPARs. In the synthesis methods disclosed herein, as depicted in FIG. 5, a modified adamantane derivative 502 is selected ensuring the amine tail of the molecule satisfied a length corresponding to AMPAR binding. The specific binding properties of the precursor compound 502 with AMPARs were not previously known. While adamantane derivatives are known generally to bind to calcium permeable AMPARs, compound 502 had not yet been studied for those purposes and has only seldomly been used in scientific research. Moreover, adamantane derivatives in general are not common to radiolabel with [$^{18}$F] because there are no halogen-group atoms to replace in the molecule. A radiochemistry leaving group, tosylate, is used on the far end of adamantane in compound 502, to facilitate novel [$^{18}$F] radiolabeling at this structure instead of at the tail.

As depicted in FIG. 5, the present invention provides a method of producing a radiolabeled compound comprising performing a radiofluorination reaction on a first compound 502 having the following structure:

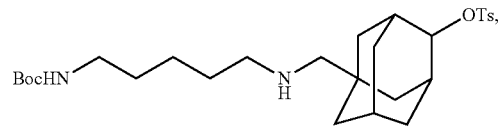 [SMILES: Cc1ccc(S(=O)(=O)OC2C3CC4CC2CC(CNCCCCCNC(=O)OC(C)(C)C)(C4)C3)cc1]

wherein OTs is tosyl and Boc is tert-Butyloxycarbonyl, so as to produce a second compound 504 having the following structure:

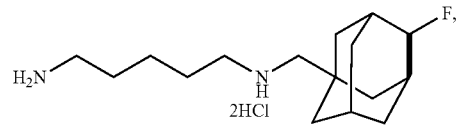

wherein the F is an [$^{18}$F] radioisotope.

In embodiments, compound 502 is [5-[[5-(tert-butoxycarbonylamino)pentylamino]methyl]-2-adamantyl] 4-methylbenzenesulfonate or (1R,3 S,5 s,7 s)-5-(((5-((tert-butoxycarbonyl)amino)pentyl)amino)methyl)adamantan-2-yl 4-methylbenzenesulfonate.

In embodiments, compound 504 is N'-[(4-fluoro-1-adamantyl)methyl]pentane-1,5-diamine or N1-(((1 s,3R,5 S,7 s)-4-fluoroadamantan-1-yl)methyl)pentane-1,5-diaminium chloride.

In embodiments, the present invention provides a method of synthesizing and/or producing a radiolabeled compound. The method comprises synthesizing an [$^{18}$F]fluoride solution comprising [$^{18}$F]fluoride via a (p,n) reaction of [$^{18}$O] water by proton bombardment in a cyclotron. In embodiments to synthesize a compound radiolabeled with a [$^{11}$C] radioisotope, this step may comprise synthesizing [$^{11}$C] carbon dioxide via a (p,n) reaction of [$^{11}$B] by proton bombardment in a cyclotron. The method of producing the radiolabeled compound further comprises extracting and/or trapping the [$^{18}$F]fluoride by passing the [$^{18}$F]fluoride solution through a preconditioned QMA anion exchange cartridge; eluting and/or heating, in a reaction vessel, the extracted [$^{18}$F]fluoride with a first solvent comprising an acetonitrile (MeCN)/water solution containing a phase transfer catalyst (e.g., potassium carbonate ($K_2CO_3$) and/or Kryptofix 2.2.2 (KF/K2.2.2); applying a vacuum to the reaction vessel so as to remove the first solvent and leave a dried residue of a [$^{18}$F]KF/K2.2.2 complex; adding, to the reaction vessel, MeCN to re-dissolve the dried residue; evaporating, via application of heat and vacuum to the reaction vessel, so as to remove residual water via azeotropic distillation leaving a second dried residue of [$^{18}$F]KF/K2.2.2 complex; mixing, in a second solvent (e.g., approximately 1 mL of a second solvent, such as MeCN or dimethyl sulfoxide (DMSO)) in the reaction vessel, the second dried residue of [$^{18}$F]KF/K2.2.2 complex and a compound 502 having the structure shown in FIG. 5; heating the reaction vessel so as to perform a radiofluorination reaction to produce a radiolabeled compound 504 having the following structure shown in FIG. 5, wherein the F is an [$^{18}$F] radioisotope; and purifying, via radio-High Performance Liquid Chromatography (HPLC), the radiofluorination reaction contents to produce a purified radiolabeled compound. In embodiments, the reaction vessel may comprise one or more different reaction vessels to which reaction contents are added. Heating a reaction vessel heats such reaction contents.

HPLC is an analytical chemistry technique used to separate, identify, and/or quantify each component in a mixture, which technique is usable here to evaluate and/or ensure purity of the radiolabeled composition. In embodiments, the method may further comprise formulating the purified radiolabeled compound in saline to prepare for human use. Purification using HPLC may be performed to prepare a solution for administration. In embodiments, the resulting purified fraction may then be reformulated for administration (e.g., injection) either by evaporating off all the solvent and replacing with saline or flowing the pure fraction through a sep-pak cartridge (e.g., C18) to trap the compound. The cartridge can then be washed with water, and the compound may be eluted off the cartridge in a low amount of ethanol. The eluted compound may be diluted with saline, e.g., such that ethanol is <10% v/v. The result may be passed through a sterile filter. In embodiments, quality control testing may be performed.

In embodiments of the present invention, a method of synthesizing a radiolabeled compound comprises obtaining (e.g., producing and/or trapping) an amount of [$^{18}$F]; eluting the [$^{18}$F] with a phase transfer catalyst KF/K2.2.2 so as to produce a solution of [$^{18}$F]KF/K2.2.2 complex; adding a first compound 502 having the structure shown in FIG. 5 to the solution of [$^{18}$F]KF/K2.2.2 complex (e.g., approximately 1 mL of the solution) so as to perform a radiofluorination reaction to create a second compound 504 having the structure shown in FIG. 5, wherein the F is an [$^{18}$F] radioisotope. In embodiments, performing the radiofluorination comprises adding heat to the reaction contents and/or to a reaction vessel containing such reaction contents. In embodiments, the method may further comprise purifying the reaction contents from to produce a purified compound radiolabeled with [$^{18}$F]. In embodiments, purifying the reaction contents can comprise performing radio-HPLC on the product of the radiofluorination reaction.

In embodiments, a method of synthesizing a radiolabeled compound comprises isolating [$^{18}$F]; combining the isolated [$^{18}$F] with a phase transfer catalyst (e.g., KF/K2.2.2) to produce an [$^{18}$F] phase transfer buffer; combining that complex with compound 502 having the structure illustrated in FIG. 5; and adding heat to produce compound 504.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The nomenclature used herein and the laboratory procedures used in analytical chemistry, radiochemistry, and organic syntheses described herein are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Agonist" refers to a chemical that binds to a receptor and activates the receptor to produce a biological response. The agonist can be endogenous, coming from within the body, or exogenous, coming from outside the body, such as a drug.

"Antagonist" refers to a chemical or drug that blocks or dampens agonist-mediated responses rather than provoking a biological response itself upon binding to a receptor. They are sometimes called blockers; examples include calcium channel blockers. In pharmacology, antagonists have affinity but no efficacy for their receptors to which they bind, and binding will disrupt the interaction and inhibit the function of an agonist.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. "Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

"Biomarker" refers to a measurable substance in an organism whose presence is indicative of some phenomenon such as disease, infection, or environmental exposure.

As used herein, "aptamer" refers to a small molecule that can bind specifically to another molecule. Aptamers are typically either polynucleotide- or peptide-based molecules. A polynucleotide aptamer is a DNA or RNA molecule that adopts a highly specific three-dimensional conformation designed to have appropriate binding affinities and specificities towards specific target molecules, such as peptides, proteins, drugs, vitamins, among other organic and inorganic molecules. Such polynucleotide aptamers can be selected from a vast population of random sequences through the use of systematic evolution of ligands by exponential enrichment. A peptide aptamer is typically a loop of about 10 to about 20 amino acids attached to a protein scaffold that binds to specific ligands. Peptide aptamers may be identified and isolated from combinatorial libraries, using methods such as the yeast two-hybrid system.

The terms "diagnose," "diagnosing," and "diagnosis," refer to detecting measures described herein. The methods of "diagnosis" can employ using detection and/or imaging techniques, such as PET scan imaging, on a subject to identify target compounds in target anatomical regions, to identify presence of and/or quantities of target compounds in target anatomical regions, to identify characteristics of target compounds in target anatomical regions, and/or to identify characteristics of target anatomical regions. This can require administration of a composition of the present invention, for example, a subject possibly afflicted with a disease or disorder, in order to detect, identify, determine the severity of, or determine the course of treatment of the disorder or recurring disorder, or in order to prolong the survival of a subject beyond that expected in the absence of such diagnosis.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity or frequency of at least one sign or symptom of the disease or disorder experienced by a patient is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "isotope" refers to any variant of a particular chemical element which differ in neutron number, although all isotopes of a given element have the same number of protons in each atom. For example, carbon-12, carbon-13 and carbon-14 are three isotopes of the element carbon with mass numbers 12, 13 and 14 respectively. "Radiolabeled" or "Radioactive" as applied to an object, sometimes called "radioisotope" refers to a composition that has excess nuclear energy, making it unstable. This excess energy can either create and emit, from the nucleus, new radiation (gamma radiation) or a new particle (alpha particle or beta particle), or transfer this excess energy to one of its electrons, causing it to be ejected (conversion electron). During this process, the object is said to undergo radioactive decay. Radioisotopes are used for diagnosis, treatment, and research. Radioactive chemical tracers emitting gamma rays or positrons can provide diagnostic information about internal anatomy and the functioning of specific organs. Radioisotopes can be attached to a ligand in order to determine receptor binding. This is used in some forms of tomography such as PET scanning.

The term "ligand" refers to any substance that forms a complex with a biomolecule, and can serve a biological purpose. In protein-ligand binding, the ligand is usually a molecule which produces a signal by binding to a site on a target protein (usually a receptor). The binding typically results in a change of conformation of the target protein. In DNA-ligand binding studies, the ligand can be a small molecule, ion or protein, that binds to a particular part of the DNA double helix. The relationship between ligand and binding partner is a function of charge, hydrophobicity, and molecular structure. In terms of ligand-receptor binding, the ligand can either be an agonist or antagonist (competitive or non-competitive) of the receptor. "Radiolabeled" or "Radioactive" as applied to an object, sometimes called "radioligand" or "tracer" refers to a biochemical substance (in particular, a ligand that is radiolabeled) that is used for diagnosis or for research-oriented study of the receptor systems of the body. In a neuroimaging application the radioligand can be injected into the pertinent tissue, or infused into the bloodstream and binds to its receptor. In embodiments, the radioligand may be administered orally via swallowing, by inhalation, by injection (intravenous), and/or by enema. When the radioactive isotope in the ligand decays, it can be measured by PET or SPECT scan imaging.

It is often used to quantify the binding of a test molecule to the binding site of radioligand.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

The term "(p,n) reaction" refers to a type of nuclear reaction that occurs when a neutron enters a nucleus and a proton leaves the nucleus simultaneously.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides. In an embodiment, a peptide is 20 amino acids or less in length. In an embodiment, a peptide is 10 amino acids or less in length.

As used herein, a "peptidomimetic" is a compound containing non-peptidic structural elements that is capable of mimicking the biological action of a parent peptide. A peptidomimetic may or may not comprise peptide bonds.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T." "Recombinant polynucleotide" refers to a polynucleotide having sequences that are not naturally joined together. An amplified or assembled recombinant polynucleotide may be included in a suitable vector, and the vector can be used to transform a suitable host cell.

The term "positron emission tomography (PET)" refers to a functional imaging technique that is used to observe metabolic processes in the body. The system detects pairs of gamma rays emitted indirectly by a positron-emitting radioisotope (tracer), which is introduced into the body on a biologically active molecule.

The term "single-photon emission computed tomography (SPECT)" is a nuclear medicine tomographic imaging technique that is used to observe metabolic processes in the body. SPECT is similar to PET in its use of radioactive tracer material and detection of gamma rays. In contrast with PET, however, the tracers used in SPECT emit gamma radiation that is measured directly, whereas PET tracers emit positrons that annihilate with electrons up to a few millimeters away, causing two gamma photons to be emitted in opposite directions.

By the term "specifically binds," as used herein, is meant a molecule, such as a ligand, which recognizes and binds to another molecule or feature, such as a receptor, but does not substantially recognize or bind other molecules or features in a sample.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists. Inhibiting a receptor means reducing a parameter of the receptor's function(s).

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "subject" or "patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

REFERENCES

1. *PTSD Statistics*, PTSD United, available at http://www.ptsdunited.org/ptsd-statistics-2/.
2. American Psychiatric Association, *Diagnostic and statistical manual of mental disorders* (5th ed), Arlington, VA, American Psychiatric Publishing (2013)
3. AMPA receptor, Wikipedia, https.//en.wikipedia.org/wiki/AMPA receptor.
4. Park et al., Calcium-Permeable AMPA Receptors Mediate the Induction of the Protein Kinase A-Dependent Component of Long-Term Potentiation in the Hippocampus, Journal of Neuroscience 13 Jan. 2016, 36 (2) 622-631.
5. Perusini, Jennifer Nicole, The Mechanisms of Fear Sensitization Caused by Acute Traumatic Stress: from Induction to Expression to Long-Lasting Reversal, UCLA: Psychology 0780 (2014), retrieved from: http://escholarship.org/uc/item/3578829d.

6. Perusini et al., Induction and Expression of Fear Sensitization Caused by Acute Traumatic Stress, Neuropsychopharmacology, 41: 45-57 (2016).
7. Rau, V., De Cola, J. P., & Fanselow, M. S. (2005). Stress-induced enhancement of fear learning: An animal model of posttraumatic stress disorder. *Neuroscience & Biobehavioral Reviews*, 29, 1207-1223.
8. Rau, V. & Fanselow, M. S. (2009). Exposure to a stressor produces a long lasting enhancement of fear learning in rats. *Stress*, 12, 25-33.
9. Bolshakov et al., Different arrangement of hydrophobic and nucleophilic components of channel binding sites in N-methyl-D-aspartate and AMPA receptors of rat brain is revealed by channel blockade, Neuroscience Letters 291 (2000) 101-104.
10. Morris et al., Diagnostic accuracy of 18F amyloid PET tracers for the diagnosis of Alzheimer's disease: a systematic review and meta-analysis, Eur J Nucl Med Mol Imaging. 2016; 43:374-385.
11. Olah et al., Ionic Fluorination of Adamantane, Diamantane, and Triphenylmethane with Nitrosyl Tetrafluoroborate/Pyridine Polyhydrogen Fluoride (PPHF), J. Org. Chem., 1983, 48 (19), pp 3356-3358 (September 1983) (DOI: 10.1021/jo00167a050).
12. Rozen and Gal, Direct Synthesis of Fluoro-Bicyclic Compounds with Fluorine, J. Org. Chem., 1988, 53 (12), pp 2803-2807 (June 1988) (DOI: 10.1021/jo00247a026).

What is claimed is:

1. A device for detecting GluA1 protein levels, or GluA1-containing AMPA receptor levels, in a portion of a brain of a subject, comprising:
a radiation sensing device to detect or quantify radiation levels associated with a radiolabeled composition comprising a ligand of GluA1 protein or a ligand of a GluA1-containing AMPA receptor; and
non-transitory computer-readable memory programmed to perform these steps:
determining or quantifying, based on a detection or quantification of a first amount of the radiolabeled composition by the radiation sensing device, a GluA1 protein level or GluA1-containing AMPA receptor level in the portion of the brain of the subject;
providing an indication of the GluA1 protein level or GluA1-containing AMPA receptor level in the portion of the brain of the subject;
comparing the GluA1 protein level or GluA1-containing AMPA receptor level in the portion of the brain of the subject to a control level of GluA1 protein or GluA1-containing AMPA receptors; and
generating a visual representation of the results of the comparing step.

2. The device of claim 1, wherein the control level is determined by determining or quantifying, based on a second detection or quantification of a second amount of the radiolabeled composition by the radiation sensing device, a second GluA1 protein level or GluA1-containing AMPA receptor level in a reference brain region of the subject.

3. The device of claim 1, wherein the control level is a predetermined and preprogrammed baseline level of GluA1 protein or GluA1-containing AMPA receptors.

4. The device of claim 1, wherein the device is further programmed to provide an indication or notification that the GluA1 protein level or GluA1-containing AMPA receptor level in the portion of the brain of the subject exceeds the control level of GluA1 subunits or GluA1-containing AMPA receptors.

5. The device of claim 1, wherein the comparing step further comprises determining whether the GluA1 protein level or the GluA1-containing AMPA receptor level in the portion of the brain of the subject exceeds the control level of GluA1 protein or GluA1-containing AMPA receptors by at least a threshold amount.

6. The device of claim 5, wherein the threshold amount is programmed as a percentage of the control level of GluA1 protein or GluA1-containing AMPA receptors or as a numeric amount of GluA1 protein or GluA1-containing AMPA receptors.

7. The device of claim 1, wherein the portion of the brain of the subject is an amygdala.

8. The device of claim 7, wherein the GluA1 protein level or GluA1-containing AMPA receptor level in the amygdala of the subject greater than the control level of GluA1 protein or GluA1-containing AMPA receptors indicates Post-Traumatic Stress Disorder (PTSD) in the subject.

9. The device of claim 8, wherein the device is further programmed to provide an indication or diagnosis of PTSD based on the result of the comparing step.

10. The device of claim 7, wherein the visual representation of the results of the comparing step comprises a first visual representation of the amygdala of the subject showing the GluA1 protein level or GluA1-containing AMPA receptor level in the amygdala of the subject and further comprises a second visual representation of the control level of GluA1 protein or GluA1-containing AMPA receptors.

11. The device of claim 10, wherein the second visual representation is overlaid on the first visual representation.

12. The device of claim 1, wherein the visual representation of the results of the comparing step comprises an artistic rendering of the brain of the subject.

13. The device of claim 1, wherein the radiation sensing device comprises a camera.

14. The device of claim 1, wherein the device is a portable electronic device.

15. The device of claim 1, wherein the subject is a living subject.

16. The device of claim 1, wherein the device is further programmed to produce pictures based on detection of radiation from the radiolabeled composition.

17. The device of claim 1, wherein the device is further programmed to indicate locations of detected radiation from the radiolabeled composition within an area to be imaged.

18. The device of claim 1, wherein the first amount of the radiolabeled composition is an amount of the radiolabeled composition that has undergone uptake and accumulation in the portion of the brain of the subject by binding to GluA1 protein or GluA1-containing, GluA2-lacking AMPA receptors after administration of an initial amount of the radiolabeled composition.

19. The device of claim 1, wherein the programmed step of determining or quantifying a GluA1 protein level or GluA1-containing AMPA receptor level in the portion of the brain of the subject comprises using an uptake value.

20. The device of claim 1, wherein the device is usable for radiological imaging.

* * * * *